(12) United States Patent
Kim

(10) Patent No.: US 9,353,806 B2
(45) Date of Patent: May 31, 2016

(54) METHOD OF ESTIMATING TORQUE OF TRANSMISSION CLUTCH

(71) Applicants: Hyundai Motor Company, Seoul (KR); Kia Motors Corp., Seoul (KR)

(72) Inventor: Jin Sung Kim, Seoul (KR)

(73) Assignees: Hyundai Motor Company, Seoul (KR); Kia Motors Corp., Seoul (KR)

( * ) Notice: Subject to any disclaimer, the term of this patent is extended or adjusted under 35 U.S.C. 154(b) by 0 days.

(21) Appl. No.: 14/475,203

(22) Filed: Sep. 2, 2014

(65) Prior Publication Data

US 2015/0167758 A1    Jun. 18, 2015

(30) Foreign Application Priority Data

Dec. 13, 2013    (KR) ........................ 10-2013-0155750

(51) Int. Cl.

| | |
|---|---|
| *B60W 10/06* | (2006.01) |
| *B60W 10/11* | (2012.01) |
| *F16D 48/06* | (2006.01) |
| *G01L 3/00* | (2006.01) |
| *A61B 6/04* | (2006.01) |
| *G01L 1/22* | (2006.01) |
| *G01L 1/24* | (2006.01) |

(52) U.S. Cl.
CPC . *F16D 48/06* (2013.01); *A61B 6/04* (2013.01); *G01L 1/2206* (2013.01); *G01L 1/246* (2013.01); *G01L 3/00* (2013.01); *F16D 2500/3067* (2013.01); *F16D 2500/3165* (2013.01); *F16D 2500/7048* (2013.01); *F16D 2500/7061* (2013.01); *F16D 2500/70247* (2013.01); *F16D 2500/70668* (2013.01)

(58) Field of Classification Search
None
See application file for complete search history.

(56) References Cited

U.S. PATENT DOCUMENTS

| | | | |
|---|---|---|---|
| 6,364,809 B1 | 4/2002 | Cherry | |
| 2004/0214687 A1* | 10/2004 | Morisawa | B60W 10/06 477/109 |
| 2005/0255964 A1* | 11/2005 | Heap | B60K 6/445 477/3 |

FOREIGN PATENT DOCUMENTS

| | | |
|---|---|---|
| JP | 6-221419 A | 8/1994 |
| JP | 2006-523292 A | 10/2006 |

(Continued)

OTHER PUBLICATIONS

Bahram Shafai et al., Design of PI Observer for Bilinear Systems with Unknown Input Disturbance, 2012 IEEE International Conference on Control Application, Oct. 3-5, 2012, Dubrovnik, Croatia.

*Primary Examiner* — Edwin A Young
(74) *Attorney, Agent, or Firm* — Morgan, Lewis & Bockius LLP

(57) ABSTRACT

A method of estimating a torque of a transmission clutch may include adjusting an error, deducing an estimated engine angular speed and deducing an estimated clutch torque. The error may be adjusted by deducing an engine transient torque based on an engine angular speed measured using a sensor, an engine static torque deduced using a data map and a load torque depending on a driving load. The estimated engine angular speed may be deduced based on the engine static torque and the engine transient torque. The estimated clutch torque may be deduced by summing an integration value and an error compensation value. The integration value and the error compensation value may be deduced based on a difference between the estimated engine angular speed and the measured engine angular speed.

8 Claims, 10 Drawing Sheets

(56) References Cited

FOREIGN PATENT DOCUMENTS

| JP | 2007-239832 A | 9/2007 |
| JP | 2008-69851 A | 3/2008 |
| JP | 2010-516957 A | 5/2010 |
| JP | 2011-089614 A | 5/2011 |
| JP | 2013-079707 A | 5/2013 |
| KR | 10-2011-0104929 A | 9/2011 |
| KR | 10-2013-0060071 A | 6/2013 |

* cited by examiner

METHOD OF ESTIMATING TORQUE OF TRANSMISSION CLUTCH

The present application claims priority of Korean Patent Application Number 10-2013-0155750 filed on Dec. 13, 2013, the entire contents of which application are incorporated herein for all purposes by this reference.

BACKGROUND OF INVENTION

1. Field of Invention

The present invention relates, in general, to a transmission clutch, and more particularly, to a method of accurately estimating the torque of a transmission clutch that is transmitted through slip in a dry clutch of a dual clutch transmission (DCT).

2. Description of Related Art

Recently, the development of dual clutch transmissions (DCTs) is actively underway since DCTs can realize not only the driving convenience of automatic transmissions but also high fuel efficiency and high power efficiency of manual transmissions. DCTs are a type of semi-automatic transmissions based on a manual transmission system, in which two torque transmission shafts are provided, and a clutch is automatically controlled without a torque converter. DCTs have an advantage of high fuel efficiency. However, in a DCT system using a dry clutch, two working parts of the clutch are directly engaged without a torque converter, and thus the start and transmission performance of a vehicle is dependent on clutch control performance. Furthermore, since it is impossible to directly measure transmission torque that occurs at the friction surface of a disk, it is important to obtain a measurement of the transmission torque of the clutch.

Among conventional methods of estimating clutch torque, there is a method of utilizing the observer theory of control engineering. This is the method of calculating transmission torque that occurs at the slipping of a clutch disk. An engine torque outputted from an electronic control unit (ECU) is based on a data obtained through repeated tests in a static state. However, a point of time when clutch torque information is required always corresponds to a transient state (creep, departure, etc.) of the engine, and thus there is a difference between the engine torque from the ECU and an actual torque. Therefore, an estimated clutch torque obtained based on the uncertain engine torque also has an error, which is problematic.

The present invention is directed to provide a method of estimating an accurate clutch torque by adjusting an error in an uncertain engine torque model.

The information disclosed in this Background section is only for enhancement of understanding of the general background of the invention and should not be taken as an acknowledgement or any form of suggestion that this information forms the prior art already known to a person skilled in the art.

SUMMARY OF INVENTION

Accordingly, the present invention has been made keeping in mind the above problems occurring in the related art and/or other problems, and the present invention is directed to provide a method of estimating the torque of a transmission clutch in order to estimate an accurate torque that is transmitted through slip in a dry clutch of a dual clutch transmission (DCT).

According to various aspects of the present invention, there is provided a method of estimating a torque of a transmission clutch. The method may include the following steps of: adjusting an error by deducing an engine transient torque based on an engine angular speed measured using a sensor, an engine static torque deduced using a data map and a load torque depending on a driving load; deducing an estimated engine angular speed based on the engine static torque and the engine transient torque; and deducing an estimated clutch torque resulted from slipping of the transmission clutch by summing an integration value and an error compensation value, wherein the integration value and the error compensation value are deduced based on a difference between the estimated engine angular speed and the measured engine angular speed.

According to an aspect of the present invention, the method may further include feeding-back the estimated clutch torque, wherein the deducing of the estimated engine angular speed is based on the engine static torque, the engine transient torque and the estimated clutch torque.

The step of adjusting the error may include deducing an engine output torque through differential of the engine angular speed and based on an engine momentum of inertia, wherein the deducing of the engine transient torque is based on the engine output torque, the engine static torque and the load torque. The engine transient torque may be deduced by subtracting the engine static torque from the engine output torque and adding the load torque to a resultant torque.

The step of adjusting the error may include deducing a final result of the engine transient torque through low-pass filtering of the deduced engine transient torque. The estimated engine angular speed may be deduced by summing the engine static torque and the engine transient torque and based on an engine momentum of inertia.

According to the method of estimating the torque of a transmission clutch of the present invention, it is possible to estimate an accurate torque that is transmitted through slip in a clutch, in particular, a dry clutch of a DCT.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION

Figure 1:
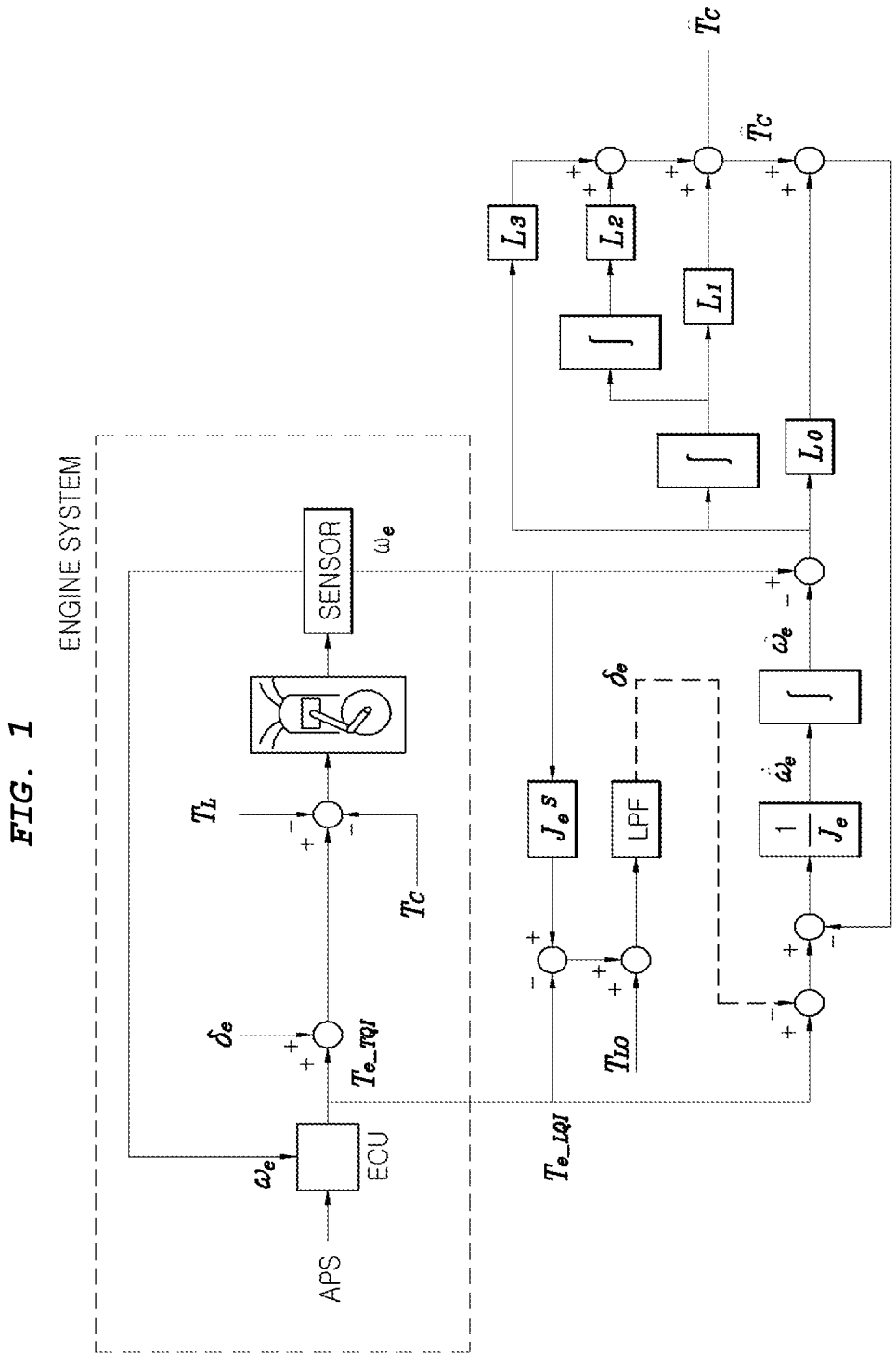
FIG. 1 is a block diagram showing an exemplary method of estimating a clutch torque according to the present invention.

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Wherever possible, the same reference numerals will be used throughout the drawings and the description to refer to the same or like parts.

Figure 2:
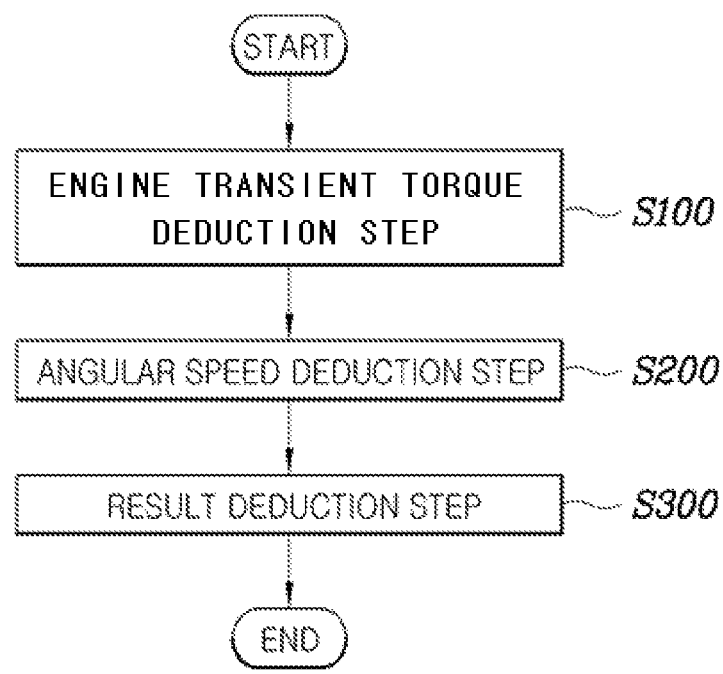
FIG. 2 is a flowchart showing an exemplary method of estimating a clutch torque according to the present invention.
Figure 3A:
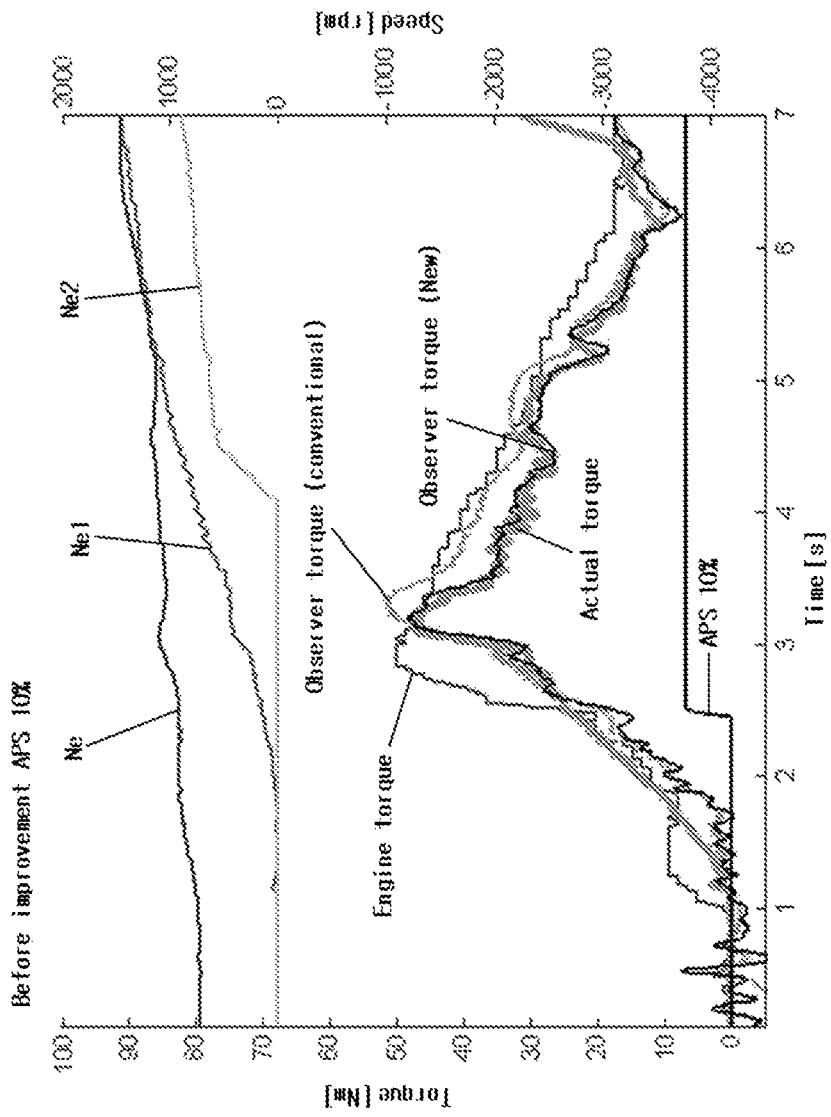
FIGS. 3A, 3B, 4A, 4B, 5A, 5B, 6A and 6B are graphs showing the effects of an exemplary method of estimating a clutch torque according to the present invention.
Figure 3B:
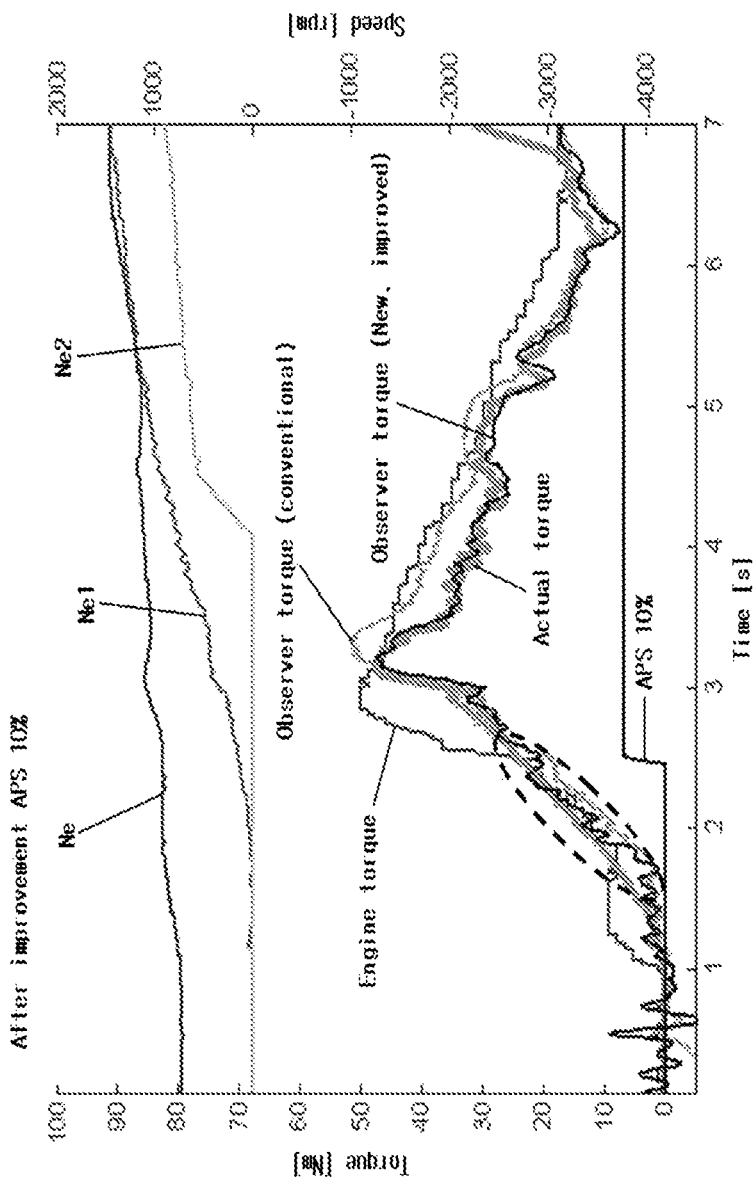
Figure 4A:
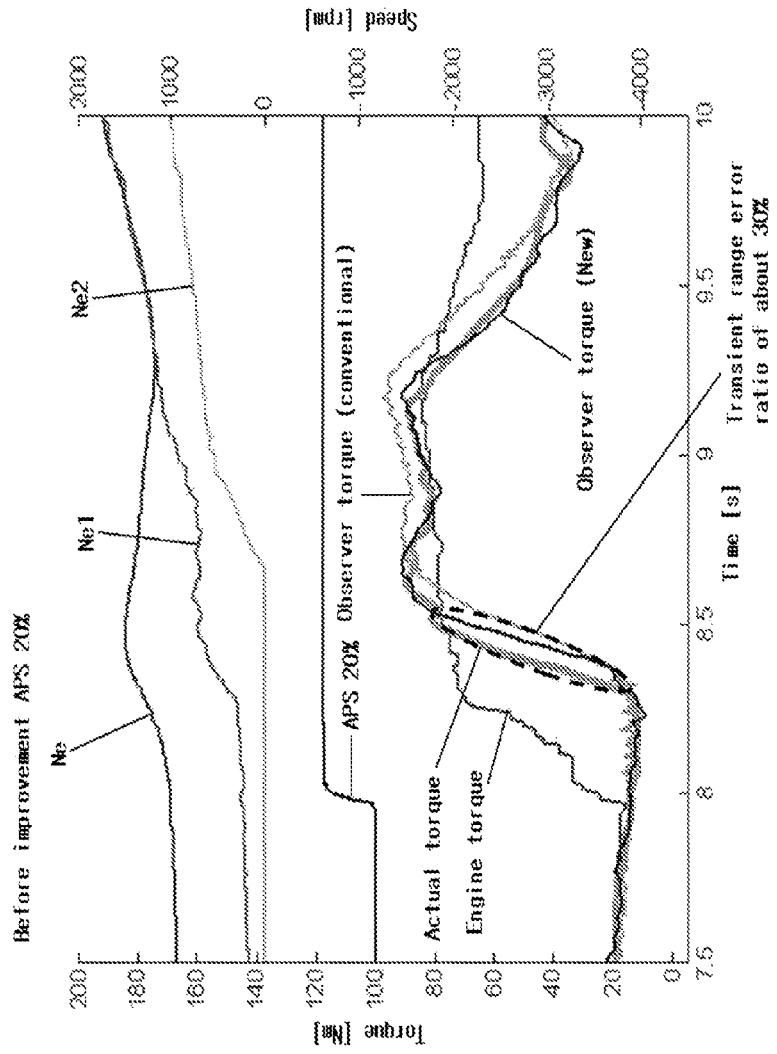
Figure 4B:
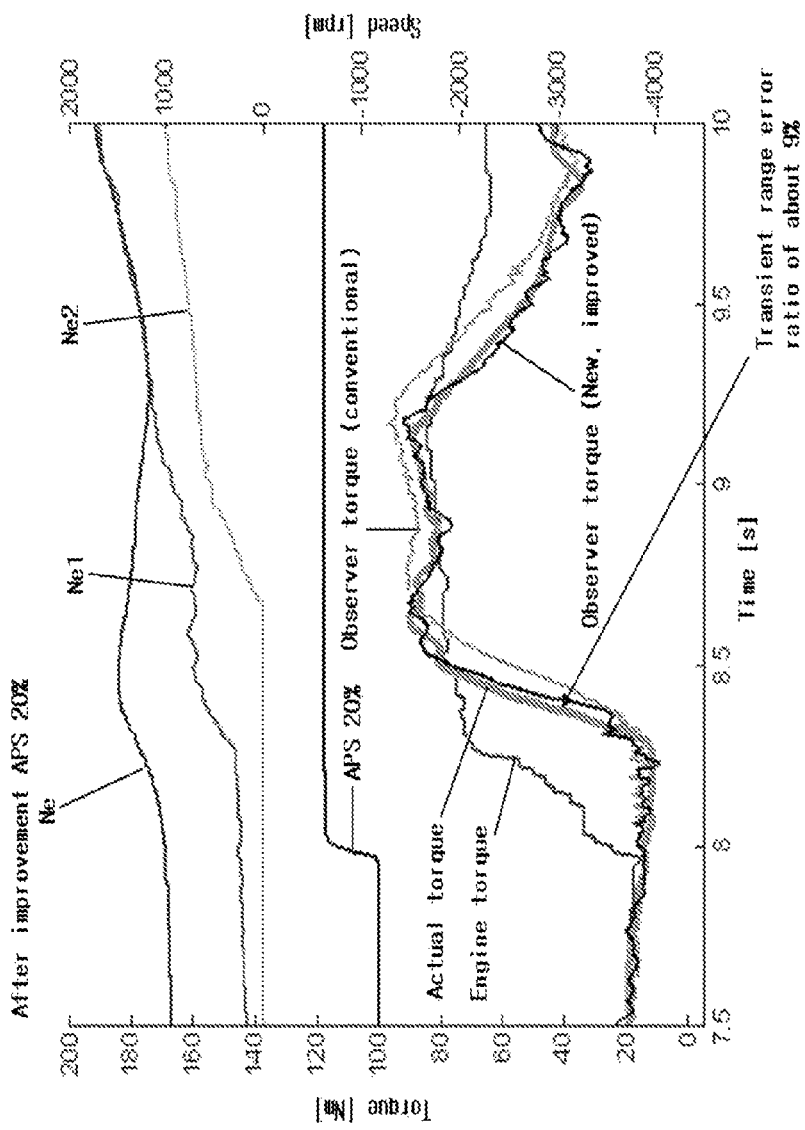
Figure 5A:
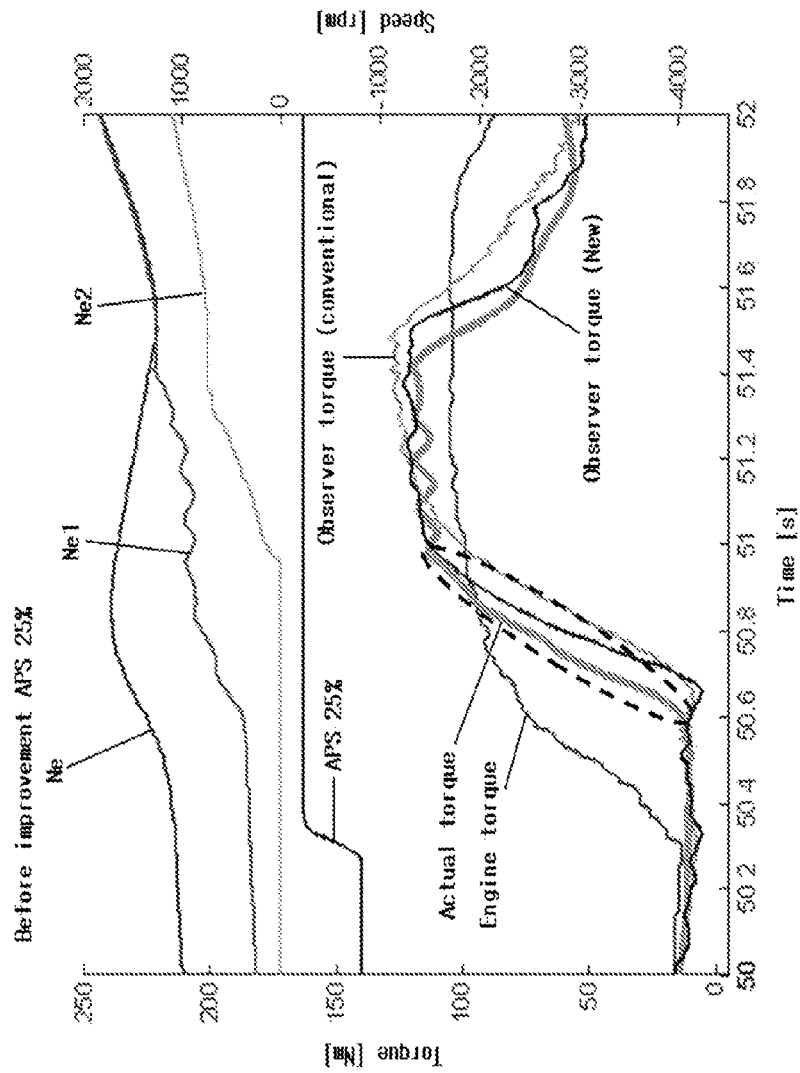
Figure 5B:
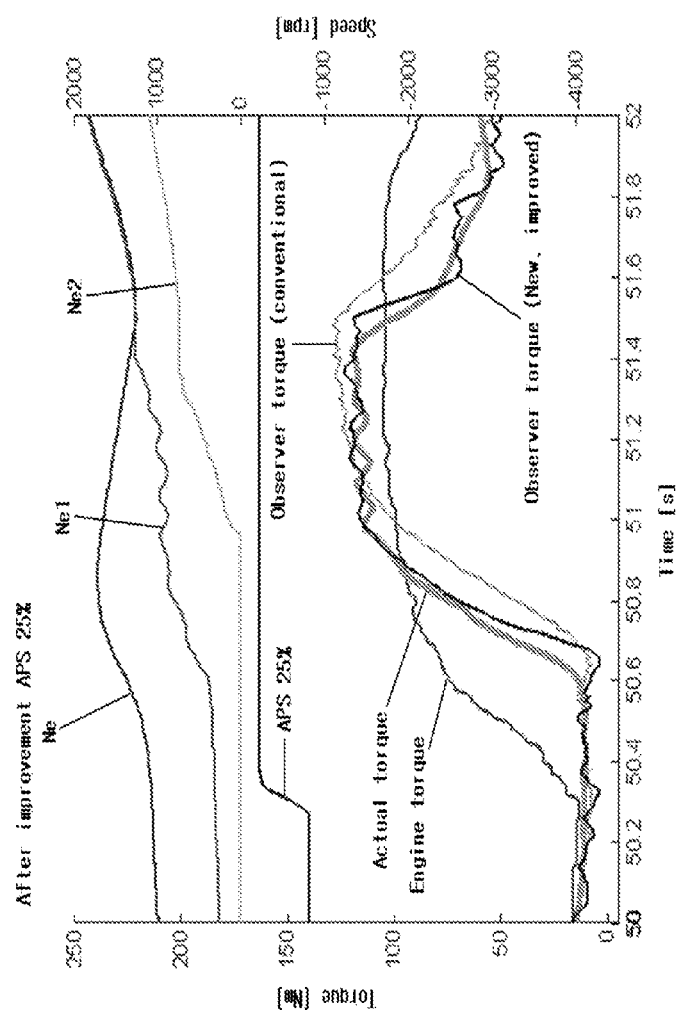
Figure 6A:
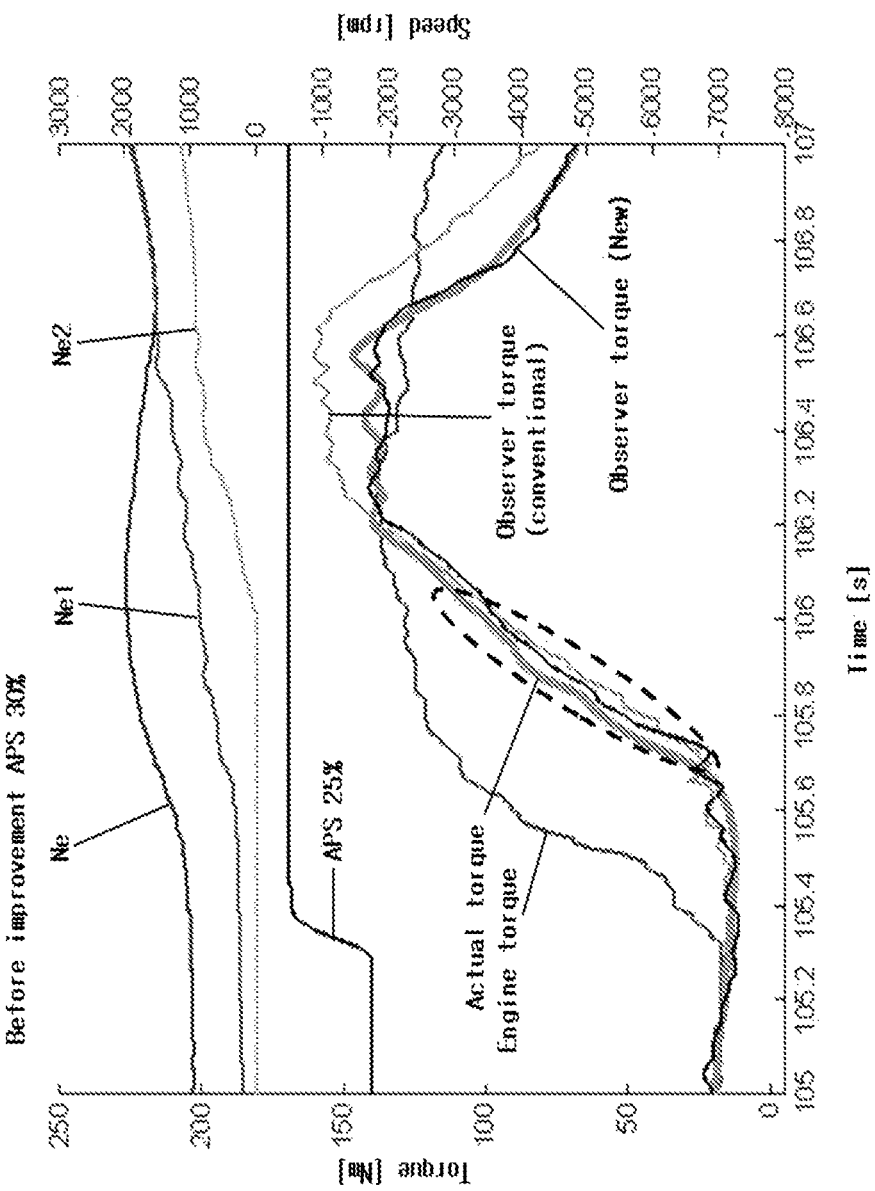
Figure 6B:
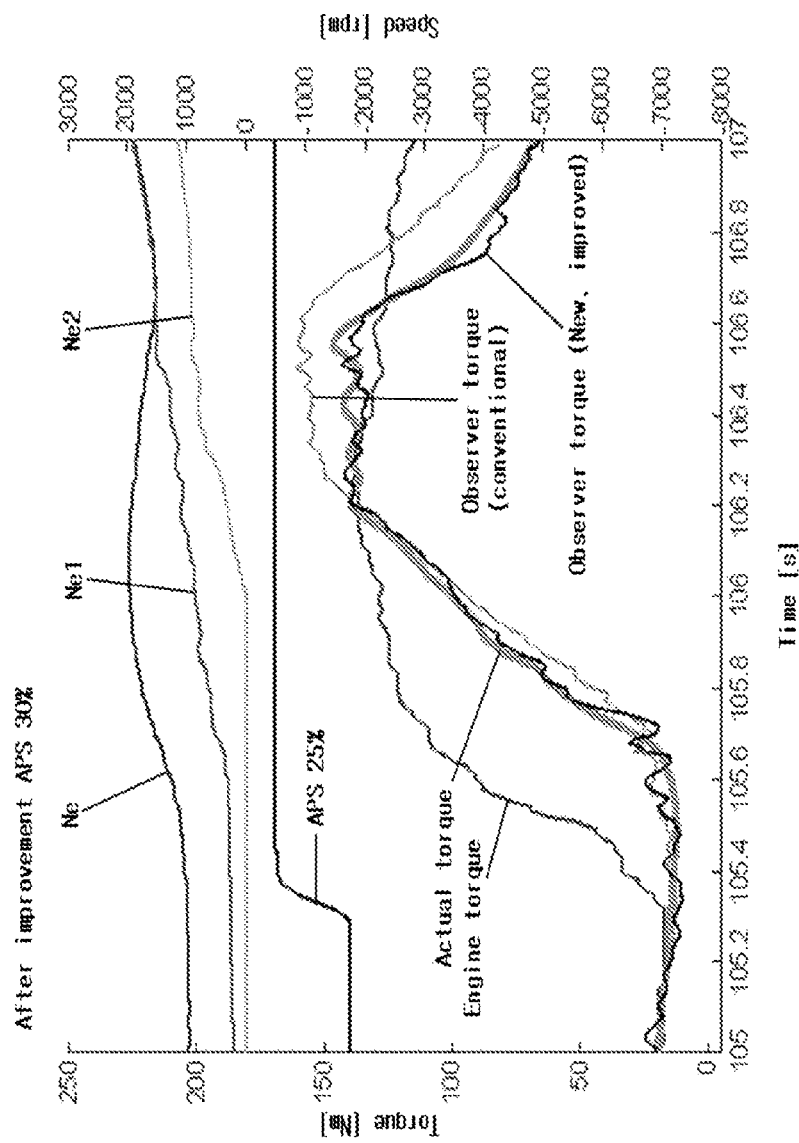

FIG. 1 is a block diagram showing a method of estimating a clutch torque according to various embodiments of the present invention, FIG. 2 is a flowchart showing a method of estimating a clutch torque according to various embodiments of the present invention, and FIGS. 3A, 3B, 4A, 4B, 5A, 5B, 6A and 6B are graphs showing the effects of a method of estimating a clutch torque according to various embodiments of the present invention.

The method of estimating the torque of a transmission clutch according to this exemplary embodiment includes an engine transient torque deduction step S100 of deducing an engine transient torque based on an engine angular speed measured using a sensor, an engine static torque deduced using a data map and a load torque depending on a driving load; an angular speed deduction step S200 of deducing an estimated engine angular speed (or reconstructed engine speed) based on the engine static torque and the engine transient torque; and a result deducing step S300 of deducing an estimated clutch torque resulting from the slipping of a transmission clutch based on the difference between the estimated engine angular speed and the engine angular speed.

Referring to the block diagram in FIG. 1, considering an engine system in terms of dynamics, an engine torque from EMS (Engine Management System) or engine static torque $T_{e\_TQI}$ and an engine transient torque $\delta_e$ is a total torque generated from an engine. An actual load torque $T_L$ incurs a loss due to the driving load, and an actual clutch torque $T_C$ incurs a loss due to the slipping of the transmission clutch. Then, the resultant torque is outputted toward a flywheel. The flywheel is provided with a speed sensor, which measures an actual engine angular speed $\omega_e$.

A pedal pressing amount and an engine angular speed $\omega_e$, which is measured using a speed sensor at the flywheel side, are inputted and then substituted to a data map which is previously provided as test values in an engine electronic control unit (ECU). In this manner, it is possible to deduce an engine static torque $T_{e\_TQI}$ in the steady state. Then, the engine static torque $T_{e\_TQI}$ and the engine transient torque $\delta e$ are summed into the actual engine driving torque.

Therefore, it is required to accurately estimate and reflect the engine transient torque in the transient state that frequently occurs in a low RPM range of the engine in order to accurately estimate a clutch slip torque. In this manner, it is possible to estimate accurate clutch torque. This has a great effect on the durability of the clutch, in particular, in control over the dry clutch of a dual clutch transmission (DCT).

An arrangement about engine dynamics can be expressed by the following formula 1:

$$J_e \dot{\omega}_e = T_{e\_TQI} + \delta_e - T_C - T_L \qquad \text{Formula 1}$$

where $J_e$ is an engine momentum of inertia, $\omega_e$ is an engine angular speed, $T_{e\_TQI}$ is engine static torque, $\delta_e$ is an engine transient torque, $T_C$ is an clutch torque, and $T_L$ is a vehicle load.

In FIG. 1, where $\omega_e$ is an engine angular speed, $\hat{\omega}_e$ is an estimated engine angular speed, $\delta_e$ is an engine transient torque, $\hat{\delta}_e$ is an estimated engine transient torque, $T_C$ is an clutch torque, $T_L$ is a vehicle load, and $T_{e\_TQI}$ is engine static torque or engine torque from EMS, $T_{L0}$ is a nominal vehicle load (value calculated using the formula of driving load).

Specifically, as shown in FIG. 1, the engine transient torque deduction step S100 of deducing the engine transient torque $\hat{\delta}_e$ is carried out based on the engine angular speed $\omega_e$ measured using the sensor, the engine static torque $T_{e\_TQI}$ deduced using the data map and the load torque based on the driving load. The engine transient torque deduction step can deduce engine output torque through the differential of the engine angular speed and based on the engine momentum of inertia, and deduce the engine transient torque based on the engine output torque, the engine transient torque and the load torque. In addition, the engine transient torque deduction step can deduce the engine transient torque by removing the engine static torque from the engine output torque and adding the load torque thereto.

In addition, the error adjustment step can deduce a final result of the engine transient torque through low-pass filtering of the deduced engine transient torque.

That is, the actual torque of the engine output terminal is obtained by integrating the measured engine angular speed $\omega_e$ and multiplying the integrated engine angular speed with the engine momentum of inertia. Then, the engine static torque $T_{e\_TQI}$ resulting from the data map is removed from the engine actual torque. In addition, the engine transient torque $\hat{\delta}_e$ can be produced by adding the load torque $T_{L0}$ due to the calculated driving load. Since the engine operates within the range of a specific frequency in the transient state, an intended value of engine transient torque can be accurately obtained through low-pass filtering. The obtained engine transient torque $\hat{\delta}_e$ is defined as an estimated value in the logic.

For reference, the load torque $T_{L0}$ can be calculated by the following formula:

$$T_{L0} = \left( M_v g \sin\theta + K_r M_v g \cos\theta + \frac{1}{2} \rho C_d A_F v_x^2 \right) * \frac{r_{wheel}}{i} \qquad \text{Formula 2}$$

where $M_v$ is a vehicle mass, g is gravitational acceleration, $\theta$ is a slope angle, $K_r$ is a rolling resistance coefficient, $\rho$ is an air density, $C_d$ is an air drag force coefficient, $A_F$ is a frontal area, $v_s$ is a vehicle speed, $r_{wheel}$ is an effective wheel radius, and i is a total gear ratio (transmission, final gear).

Afterwards, the angular speed deduction step S200 is carried out to deduce the estimated engine angular speed based on the engine static torque and the engine transient torque. The estimated engine angular speed can be deduced by considering the engine static torque, the engine transient torque and the estimated clutch torque together through the feedback of the estimated clutch torque that is estimated at the result deduction step.

In addition, the angular speed deduction step can deduce the estimated engine angular speed in a reverse manner by summing the engine static torque and the engine transient torque and using the engine momentum of inertia.

That is, the total torque of the engine is produced by summing the estimated engine transient torque value $\hat{\delta}_e$ and the engine transient torque $T_{e\_TQI}$. The total torque of the engine is divided with the engine momentum of inertia Je, followed by integration, thereby producing an estimated engine angular speed $\hat{\omega}_e$.

On the theoretical assumption that the influence of the clutch torque is reflected on the difference between the actually-measured engine angular speed $\omega_e$ and the estimated engine angular speed $\hat{\omega}_e$, the estimated clutch torque $\hat{T}_C$ can be produced based on the integration of the difference and using the coefficients $L_1$ and $L_2$. In addition, according to some embodiments, an error compensation value is deduced by multiplying the difference between the engine angular speed $\omega_e$ and the estimated engine angular speed $\hat{\omega}_e$ with the coefficient $L_3$. Then, the estimated clutch torque $\hat{T}_C$ is obtained by summing the deduced error compensation value and the integrated value. In this manner, a more reliable estimated value in the low torque range can be obtained.

The estimated clutch torque $\hat{T}_C$ is fed back together with the difference between the actually-measured engine angular speed $\omega_e$ and the estimated engine angular speed $\hat{\omega}_e$, and then is used for the deduction of the estimated clutch torque.

As shown in FIG. 1, the value that is fed back is removed or subtracted from the total of the engine static torque $T_{e\_TQI}$ and the engine transient torque $\delta_e$, and then the estimated engine angular speed $\hat{\omega}_e$ is deduced. In this manner, repeated feedback causes conversion into an accurate estimated clutch torque.

In this feedback control, the coefficients $L_0$, $L_1$, $L_2$ and $L_3$ exist or function as tuning factors.

FIGS. 3A, 3B, 4A, 4B, 5A, 5B, 6A and 6B are graphs showing the effects of the method of estimating a clutch torque according to various embodiments of the present invention. These figures show the difference between a conventional estimated torque and an estimated torque of the present invention at several amounts of APS, e.g. pedal pressing amounts of 10%, 20%, 25% and 30%. In these graphs, the observer torque (conventional) presents an estimated clutch torque when the result deduction step is not carried out. The observer torque (new) presents a result to which an error compensation value is not added at the result detection step. The observer torque (new, improved) presents a complete result according to an example of the present invention in which the error compensation value is added at the result deduction step. As apparent from these results of the graphs, the present invention can obtain an estimated clutch torque that is closer to the actually measured value.

According to the present invention as set forth above or the like, it is possible to adjust the error between an ECU engine torque and an actual engine torque in real time for use in the estimation of the clutch torque, and estimate an accurate clutch torque in a driving range in which the engine torque is uncertain. In addition, it is possible to promote an improvement in reliability and accuracy over the conventional engine torque-based method, and engine torque error adjustment logic can be omitted in a normal state.

There is an advantage in that information between a clutch torque and a clutch actuator position (a torque-stroke diagram) is not required.

In particular, the present invention is advantageous as the accuracy of conventional art in a low engine RPM range (low engine torque range of 1000 RPM or less or APS 30% or less) is low. The sensibility to variations in the engine dynamics is raised through direct feedback of the engine RPM. In the low engine RPM range, the error rate is reduced by 20% or more than a feedback method in which the engine RPM is integrated.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method of estimating a torque of a transmission clutch, comprising:
    deducing, by a controller, an engine transient torque based on an engine angular speed measured using a sensor, an engine static torque deduced using a data map and a load torque depending on a driving load;
    deducing, by the controller, an estimated engine angular speed based on the engine static torque and the engine transient torque;
    deducing, by the controller, an estimated clutch torque resulted from slipping of the transmission clutch by summing an integration value and an error compensation value, wherein the integration value and the error compensation value are deduced based on a difference between the estimated engine angular speed and the measured engine angular speed; and
    controlling, by the controller, the transmission clutch by using the estimated clutch torque.

2. The method according to claim 1, further comprising:
    feeding-back the estimated clutch torque, wherein the deducing of the estimated engine angular speed is based on the engine static torque, the engine transient torque and the estimated clutch torque.

3. The method according to claim 1, wherein the deducing of the engine transient torque comprises:
    deducing an engine output torque through differential of the engine angular speed and based on an engine momentum of inertia, wherein the deducing of the engine transient torque is based on the engine output torque, the engine static torque and the load torque.

4. The method according to claim 3, wherein the engine transient torque is deduced by subtracting the engine static torque from the engine output torque and adding the load torque to a resultant torque.

5. The method according to claim 1, wherein the deducing of the engine transient torque comprises:
    deducing a final result of the engine transient torque through low-pass filtering of the deduced engine transient torque.

6. The method according to claim 1, wherein the estimated engine angular speed is deduced by summing the engine static torque and the engine transient torque and based on an engine momentum of inertia.

7. The method according to claim 1, wherein an error compensation value is deduced by multiplying the difference between the estimated engine angular speed and the engine angular speed with a torque observer gain.

8. A method of estimating a torque of a transmission clutch, comprising:
    deducing, by a controller, an engine transient torque corresponding to an engine output torque in a transient state;
    deducing, by the controller, an estimated engine angular speed based on an engine static torque and the engine transient torque;
    deducing, by the controller, an estimated clutch torque resulted from slipping of the transmission clutch by summing an integration value and an error compensation value, wherein the integration value and the error compensation value are deduced based on a difference between the estimated engine angular speed and an engine angular speed measured by a sensor; and controlling, by the controller, the transmission clutch by using the estimated clutch torque.

* * * * *